United States Patent [19]

Hintsche et al.

[11] Patent Number: 5,670,031
[45] Date of Patent: Sep. 23, 1997

[54] ELECTROCHEMICAL SENSOR

[75] Inventors: Rainer Hintsche, Berlin; Manfred Paeschke, Basdorf; Uwe Schnakenberg; Ulla Wollenberger, both of Berlin, all of Germany

[73] Assignee: Fraunhofer-Gesellschaft zur angewandten Forschung e.V., Munich, Germany

[21] Appl. No.: 553,266

[22] PCT Filed: May 21, 1994

[86] PCT No.: PCT/DE94/00598

§ 371 Date: Nov. 22, 1995

§ 102(e) Date: Nov. 22, 1995

[87] PCT Pub. No.: WO94/29708

PCT Pub. Date: Dec. 22, 1994

[30] Foreign Application Priority Data

Jun. 3, 1993 [DE] Germany .................... 43 18 519.3

[51] Int. Cl.[6] ................................... G01N 27/26
[52] U.S. Cl. .................. 204/412; 204/403; 204/416; 204/418; 204/409; 422/68.1; 422/82.01; 422/82.02; 422/82.03; 422/98
[58] Field of Search ........................ 204/403, 412, 204/416, 418, 409; 422/68.1, 82.01, 82.02, 82.03, 98

[56] References Cited

U.S. PATENT DOCUMENTS

| 4,900,405 | 2/1990 | Otagawa et al. | 204/412 |
| 5,034,192 | 7/1991 | Wrighton et al. | 204/418 |
| 5,290,420 | 3/1994 | Matson | 204/403 |
| 5,312,762 | 5/1994 | Guiseppei-Elie | 436/149 |
| 5,425,869 | 6/1995 | Noding et al. | 204/418 |

FOREIGN PATENT DOCUMENTS

| A-90 15323 | 12/1990 | WIPO . |
| A-93 06237 | 4/1993 | WIPO . |

OTHER PUBLICATIONS

Sensors and Actuators, vol. 15 No. 4, Dec. 1988, Lausanne, pp. 337–345 Sinclair Yee, et al. "Miniature Liquid Junction Reference Electrode with Micromachined Silicon Activity".

Analytical Chemistry, vol. 62, 1990, Columbus, OH; pp. 407–409 Tomokazu Matsue et al. "Multichannel Electrochemical Detection System for Flow Analysis" No month available.

Analytical Chemistry, vol. 64, 1992, Columbus, OH., pp. 1118–1127, I. Fritsch–Faules, et al. "Use of Microelectrode Arrays to Determine Concentration Profiles of Redox Centers in Polymer Films" No month available.

Analytical Chemistry, vol. 62, 1990, Columbus, OH., pp. 447–452; Osamu Niwa et al. "Electrochemical Behavior of Reversible Redox Species at Interdigitated Array Electrodes with Different Geometries: Consideration of Redox Cycling and Collection Efficiency" No month available.

Sensors and Actuators, B7, 1992; pp. 758–762; B. Ross et al. No month available.

*Primary Examiner*—Bruce F. Bell
*Attorney, Agent, or Firm*—Karl Hormann

[57] ABSTRACT

The invention relates to an electrochemical sensor with interdigital micro-electrodes (1) with structure widths in the sub-μm range. With a twin or multi-pair array of the interdigital micro-electrodes on a substrate (8), the electrochemical detection of molecules with high sensitivity is made possible and further uses for the detection of chemical reaction cycles are made available. The electrodes may be arranged in a micro-channel applied to the substrate having a constant small volume of a few nanoliters. The electrochemical sensor of the invention is suitable for the multiple measurement of the same species of molecule or as a multi-sensitive sensor in chemical analysis and process control in various fields such as biotechnology, environmental protection or health.

14 Claims, 4 Drawing Sheets

ELECTROCHEMICAL SENSOR

This application is a 371 of PCT/DE 94/00598 published May 21, 1994.

BACKGROUND OF THE INVENTION

1. Field of the Invention

The invention, in general, relates to an electrochemical sensor, and, more particularly, to an electrochemical sensor of the kind provided with a plurality of interdigitated micro-electrodes supported by a substrate.

Electrochemical sensors having interdigitated (i.e. interposed in the manner of fingers) micro-electrodes are usable in chemical analytics and process controls in various fields such as biotechnology, environmental protection and public health. They have small diffusion lengths for electrochemically active molecules, since the distances between individual finger-like electrode areas lie in the range of μm or sub-μm.

2. Description of the Prior Art

Electrochemical sensors with miniaturized planar electrodes with geometries in excess of 2 μm have hitherto been known. They are fabricated by thin-film technologies and are used as transductors for detecting chemical and biological substances.

Electrode geometries between 20 and 100 μm provide detection characteristics like those attainable with conventional thin-wire electrodes (vide M. Suda et al., Proceedings Second World Congress on Biosensors, Geneva, Switzerland 1992, p. 400; N. F. Sheppard, Jr. et al., Anal. Chem. 1993, 65, 1199–1202).

Arrangements comprising two parallel thin metallic film strips 5 μm wide, for measuring conductivity are known from L. D. Watson (Biosensors 3, 1987/88, 101–115).

For defining voltage profiles, T. Matsue et al. (Anal. Chem. 62, 1990, 407–409) are using an arrangement of sixteen electrodes 1 mm long and 0.1 mm wide.

An arrangement of spherical electrodes of micrometer dimensions in the insulation of a metallic surface has been described by B. Ross et al. (Sensors & Actuators B7, 1992, 758–762). Because of the electrical parallel interconnection of the micro-electrodes a measurement signal is generated only in voltammetric and chronoamperometric measurements.

I. Fritsch-Faules et al. (Anal. Chem. 64, 1992, 1118–1127) are using an arrangement of electrodes 4 μm wide and spaced 8 μm from each other, to define concentration profiles of redox centers in polymeric films.

An electrochemical sensor having a pair of interdigitated micro-electrodes is known from O. Niwa et al. (Anal. Chem. 62, 1990, 447–452). Amplification effects by electrochemical recyclization of reversible redox molecules was first shown with such sensors of structural widths between 0.75 and 10 μm.

All of the described electrodes were used in stationary measuring processes.

SUMMARY OF THE INVENTION

It is a task of the invention to provide an electrochemical sensor which makes electrochemical detection of molecules possible at a higher detection sensitivity and which offers enhanced possibilities of use for detecting chemical reaction processes.

This task is solved, in general, by an electrochemical sensor provided with two or more pairs of interdigitated micro-electrodes of structural widths less than 1 μm. The micro-electrodes are arranged as an array on a substrate. The individual pairs may be energized independently of each other with electric potentials, and the measurement effects at the individual electrodes can be drained or derived independently. In the present context, measurement effects are understood to be, in particular, amperometric, potentiometric or impedimetric effects. The preferred planar substrate used is glass, sapphire, silicon or polymers, with the electrodes being applied by planar technology. The fine geometry structuring of the electrodes results in spaces (e.g. distances of about 700 nm) between the interdigitated microelectrodes, i.e. electrodes arranged in a finger-like pattern, which are small relative to the distances traveled by the molecules to be detected, in the measuring time. Thus, it becomes possible electrochemically to capture the same molecule several times, as, for example, for repeatedly oxidizing and reducing it before it diffuses out of the range of the electrodes.

In this manner, particularly advantageous amplification effects are obtained. The multiple arrangement of finely structured pairs of electrodes in accordance with the invention advantageously leads to a multiplication of the amplification effect just described, by realizing, with an appropriate multiple electrode measuring technique (e.g. with a computer-assisted multi-potentiometer) simultaneous measurements as well as the renewed capture of molecule species which had previously been made at a neighboring interdigitated electrode pair. Simultaneous measurement and recapture lead to a significant improvement in the analytical detection sensitivity.

Additional advantageous possibilities of utilization of the sensors in accordance with the invention will be described infra.

In a currently preferred embodiment of the invention, the micro-electrodes consist of thin layers of a noble metal and/or a potential-forming metal oxide (e.g. silver—silver halogen) or metal salts. These thin layers are deposited on, or inserted into, the surface of the substrate as thin-film electrodes in such a manner that the surface is planarized and the electrodes are at the same time mechanically stabilized. The planarization results in optimizing the diffusion characteristic between adjacent electrodes.

An especially advantageous embodiment of a sensor in accordance with the invention resides in the active surfaces of the micro-electrodes being placed in a micro-channel provided with entry and exit flow openings and positioned on the substrate. The micro-channel may, for instance, be a channel or groove etched or laser-structured into silicon or polymer which is applied to the substrate by adhesion or bonding. Thus, the entire array of micro-electrodes is arranged within a defined and constant space of small volume, viz.: the micro-channel. The particular advantage of this arrangement is its constant and small volume of but a few nanoliters which surrounds the micro-electrodes and which permits measurements of the minutest changes in the substance under investigation. With interdigitated pairs of micro-electrodes serially arranged in the direction of the channel (the interdigitated electrode areas are arranged normal to the channel direction), it is possible to take simultaneous or successive measurements at different locations within the micro-channel.

Advantageously, the micro-channel is formed as an auxiliary means for immobilizing or retaining chemical or biological substances, in that polymeric films may be fixed with biocomponents by oblique or overlapping channel walls. Chemically charged micro-balls can be arrested by silicon-etched grids. Structured in this manner, the micro-channel functions as a reactor vessel.

In another embodiment of the invention, additional surface electrodes are provided as working or reference electrodes in addition to the micro-electrode arrays, for instance, as a surrounding surface.

A further advantageous embodiment of the electrochemical sensor in accordance with the invention is provided with a liquid-resistant insulation of the conductive strips which connect the micro-electrodes to contact surfaces at the margin of the substrate. The insulation comprises a layer, preferably of silicon, silicon nitride of photo resist. The insulating layer is applied in such a manner that the active surfaces of the micro-electrodes and the contact surfaces remain accessible to the analytic medium and to electrical contacting, respectively.

The electrochemical sensor in accordance with the invention may be used in many different functions. For instance, it may be used for the simultaneous multiple measuring of the same species of molecule. Thus, by multiple measurements of the same measuring effect, an average of the amperometric, potentiometric or impedimetric measuring effects may be obtained with the multiple arrangement of the interdigitated micro-electrodes. Given n number of micro-electrodes, each measuring effect is measured n times, and the signal to noise ratio, or the overall sensitivity of the entire measurement, is improved in accordance with the square root of n.

Another possibility of utilizing the sensor in accordance with the invention is the simultaneous or successive detection of different electrochemical reactions or the detection of the development over time of the same or different electrochemical reactions. By simultaneously or successively applying different potentials to the individual micro-electrodes, different electrochemical processes occurring at the respective electrodes can be detected simultaneously or successively, as the case may be. The sequential application of the potentials to spatially closely adjacent micro-electrodes additionally offers the advantageous possibility of monitoring fast reactions over time. The measuring method of pulse polarography may also be practiced by successively alternating the potentials applied to the micro-electrodes.

Advantageously, the sensor of the invention may be used for measuring the flow velocity of an analytical sample, the change in time of the sample, or the intermixing effect of the sample, by measuring electrochemically active molecules of the sample at different electrodes by localized and/or successive detection. A significant advantage in the measurement results from the micro-electrodes being provided in a micro-channel of defined and constant volume. A species is thus created at one electrode and, dependent upon the flow, is measured at another electrode. Because of the constant volume it is also possible, when the flow is stopped, to monitor changes in the sample over time or intermixing effects.

The electrochemical sensor in accordance with the invention may advantageously be utilized to prove, at a high sensitivity, the activities of enzymes which in the presence of suitable enzyme substrates catalyze the release of an electrochemically reversible product, by polarizing a micro-electrode of an interdigitated pair of micro-electrodes in such a manner that the oxidized reaction product is reduced. In this manner, it is possible with high sensitivity to detect the release of reversible oxidizable and reducible products, particularly of hydrolytic enzyme reactions, by a repeated conversion of the product of the enzyme reaction. Such a use of the sensor in accordance with the invention makes it possible with high sensitivity to define enzyme substrates, and is suitable for a highly sensitive detection of enzymes.

The enzyme itself may, for instance, be an analyte, or it may serve as a marker in immuno tests or in DNA-hybridizing methods. To this end, the enzyme or enzymes are externally incubated in a solved state or fed into the electrode chamber (e.g. the micro-channel), or they will have been arranged in the micro reaction chamber in an immobilized state.

BRIEF DESCRIPTION OF THE DRAWINGS

The arrangement in accordance with the invention will hereafter be described in more detail, on the basis of preferred embodiments with reference to the drawings, in which.

DETAILED DESCRIPTION OF PREFERRED EMBODIMENTS

Figure 1:
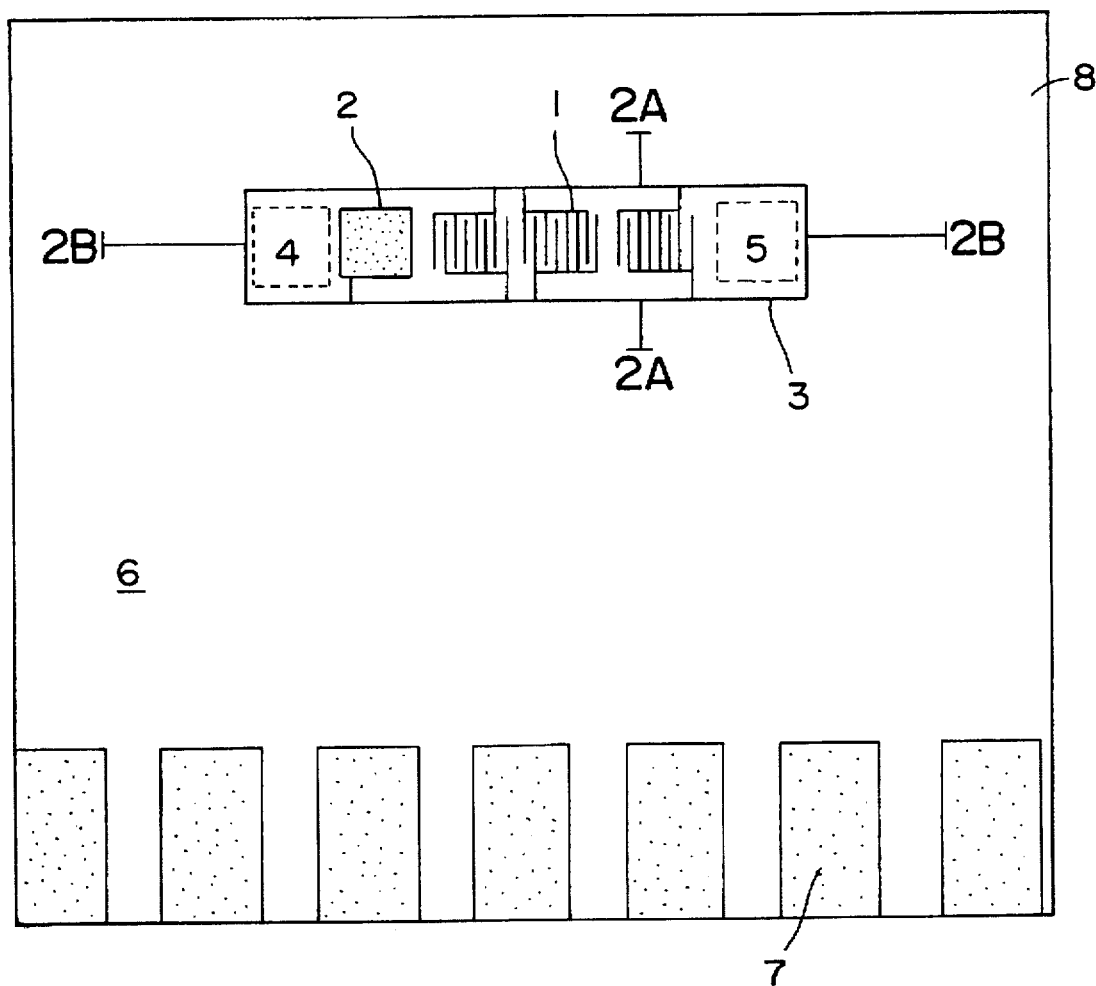
FIG. 1 schematically depicts an example of an electrochemical sensor.

An embodiment of an electrochemical sensor in accordance with the invention is depicted in FIG. 1. Pairs of interdigitated micro-electrodes 1 are arranged in a row on a planer silicon chip 8, together with a reference electrode 2. The conductors from the micro-electrodes 1 and the reference electrode 2 to electrical contact surfaces 7 are covered by an insulating layer 6.

Figure 2A:
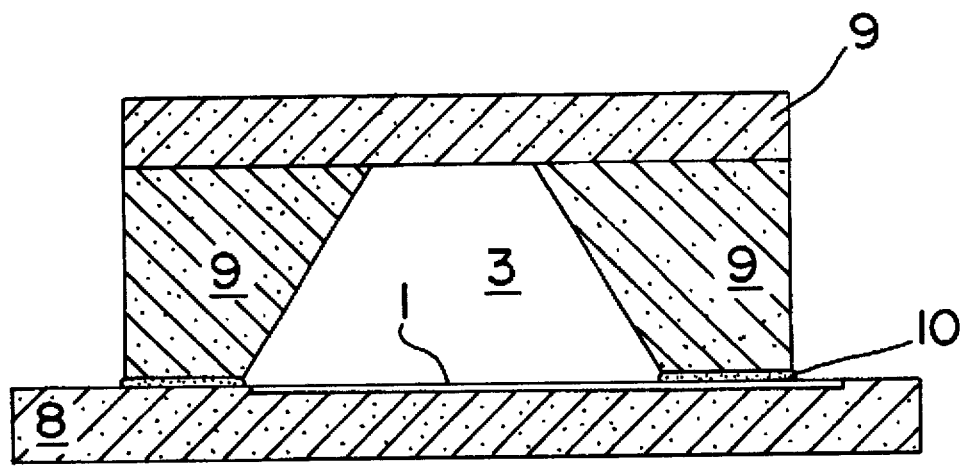
FIG. 2 schematically depicts a cross-section along line A–A' and a longitudinal section along line B–B' of the arrangement of the electrodes of the electrochemical sensor of FIG. 1, including an applied micro-channel (not shown in FIG. 1)
Figure 2B:
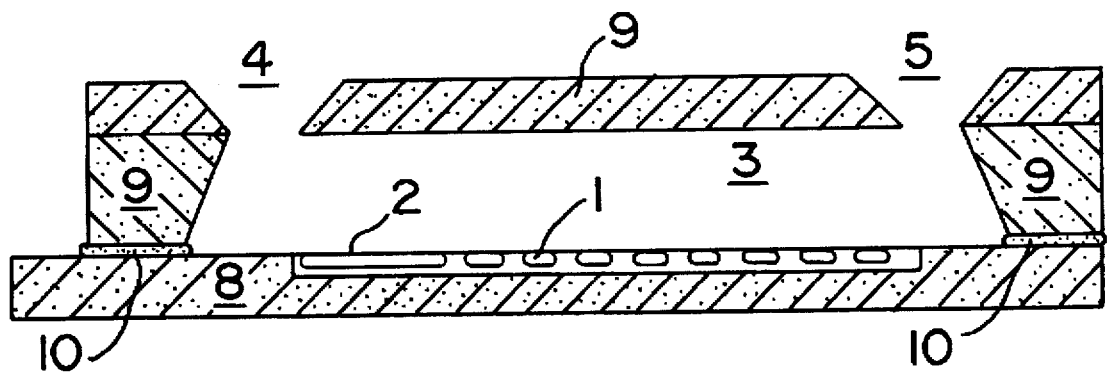

A cross-section of the electrochemical sensor along line A–A' and a longitudinal section along line B–B' in FIG. 1 is shown in FIG. 2 and is shown to include a micro-channel 3. In the embodiment shown, the micro-channel 3 is a silicon chip 9 with an anisotropically etched groove adhesively connected to the silicon chip 8 containing the micro-electrodes 1. An adhesive or sealing layer 10 is provided between the silicon chips 8 and 9. Entry and exit openings 4 and 5 of the micro-channel 3 can be seen in the longitudinal section.

Figure 3:
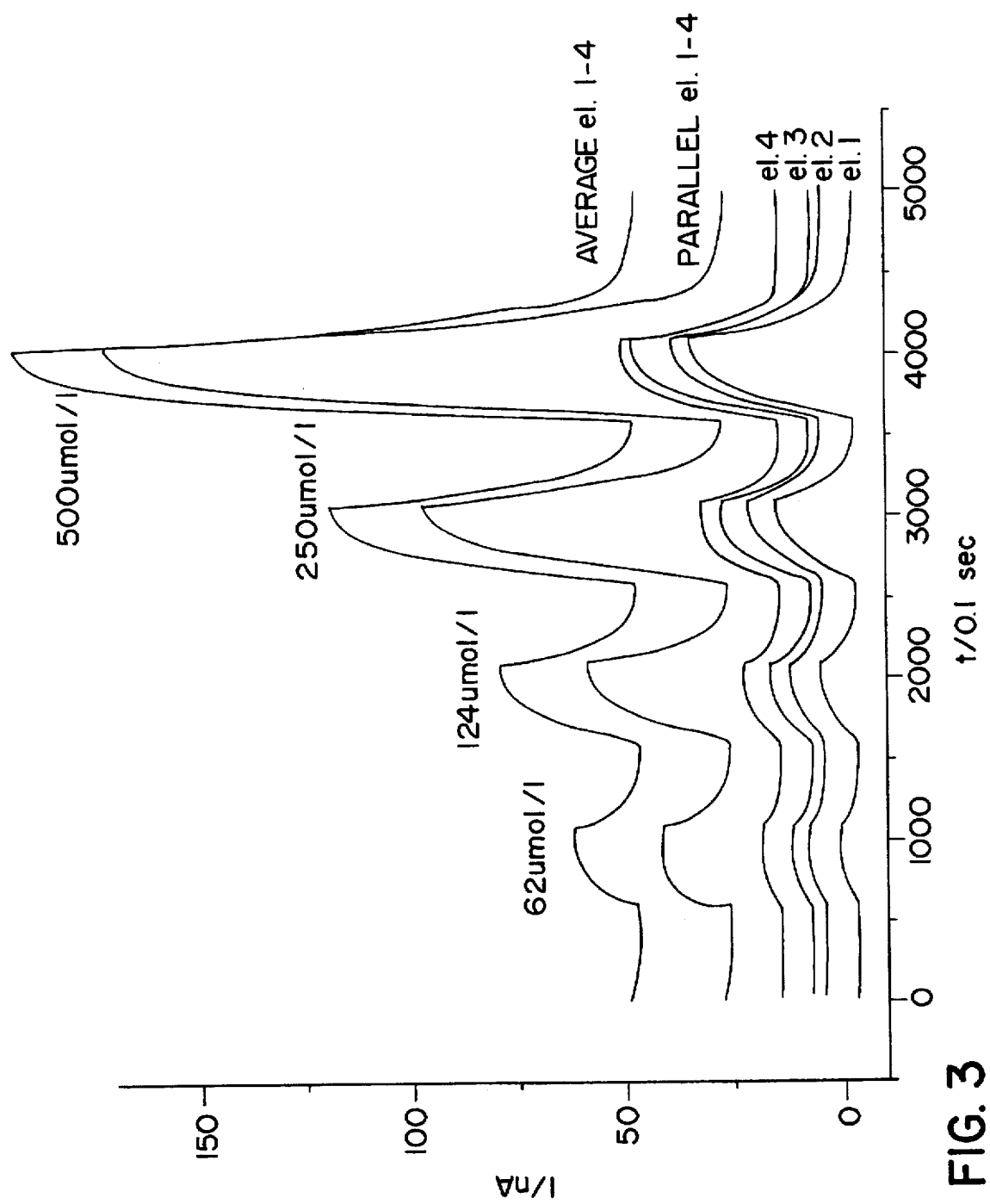
FIG. 3 represents measuring curves of the oxidation of ferrocyanide.

FIG. 3 depicts measurement curves of the oxidation of ferrocyanide taken with a sensor in accordance with the invention. The individual maximum values result after adding 62, 124, 250 and 500 µmol/l of ferrocyanide. The curves (I(t)) of simultaneous measurements of each of four micro-electrodes (el.1, el.2, el.3, el.4), the measurement curve of the parallel circuit of the four electrodes (parallel el. 1–4) and the average measuring curve resulting from the simultaneous measurement by the four electrodes (average el. 1–4) are also shown. The low signal-to-noise ratio of the simultaneous multiple measurement possible with the sensor in accordance with the invention are clearly recognizable.

Figure 4:
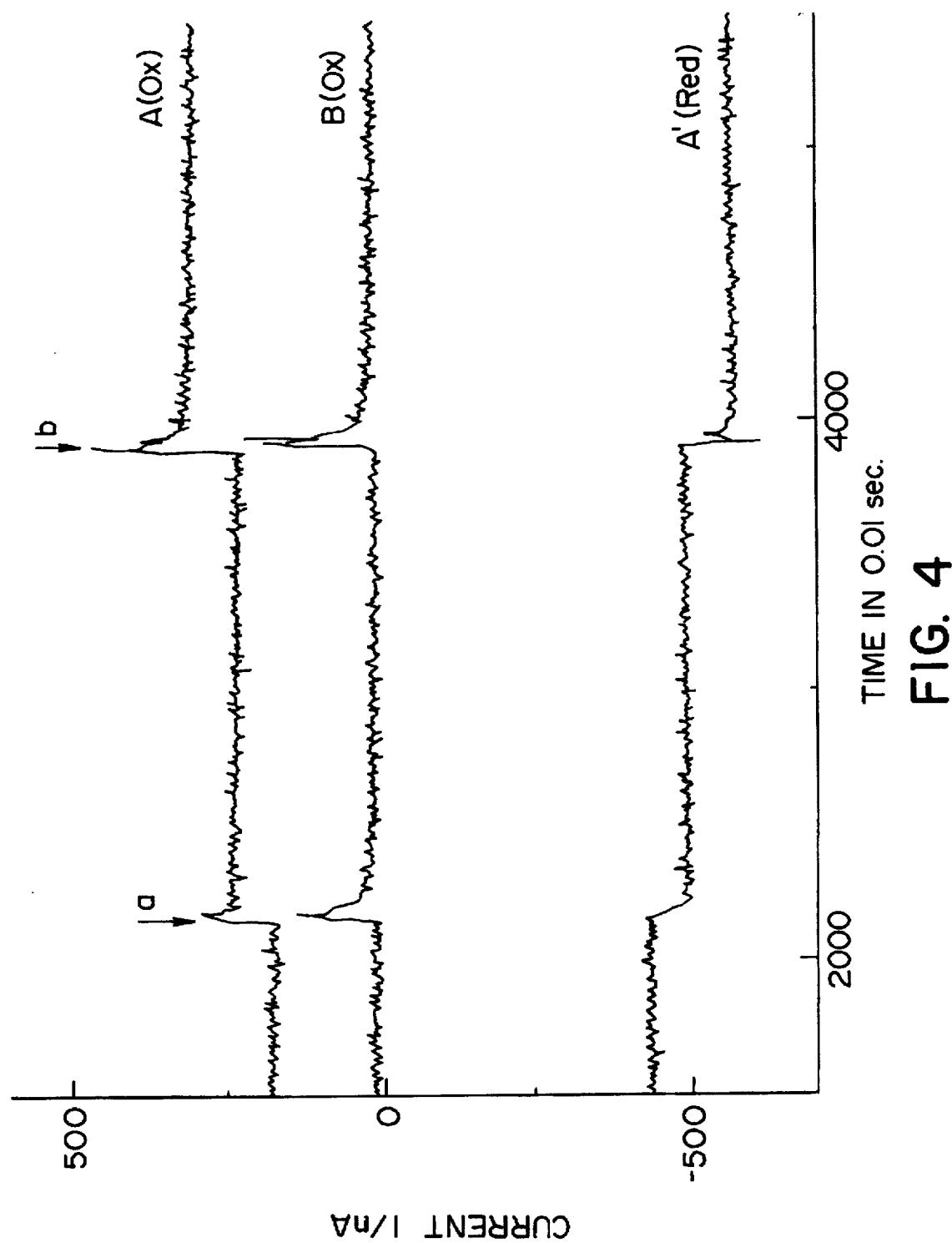
FIG. 4 represents measuring curves depicting the detection of p-aminophenol.

The amplification effect of the interdigitated arrangement of micro-electrodes is shown in FIG. 4, based upon the example of measurement curves (I(t)) derived from the detection of p-aminophenol by repeated oxidation and reduction at an interdigitated pair of electrodes (A(Ox) and A' (Red)). For comparison, measurement curve (B(Ox)) taken with conventional oxidation (the second electrode has no function) at the same pair of electrodes. (a,b: 50 µmol/l of p-aminophenol added to each). The significant differences in the signal levels depict the advantage of the interdigitated arrangement of the micro-electrodes.

The following is a description, by way of examples, of two possible uses of the electrochemical sensor in accordance with the invention.

The first example relates to the sensitive definition of the activity of alkaline phosphatase. An electrochemical sensor of the kind shown in FIGS. 1 and 2 is put into a flow system. One electrode of an interdigitated pair of electrodes is polarized to 250 mV relative to a silver/silver chloride (saturated KCl) reference electrode (positioned in the exit flow). A potential of −50 mV is applied to the other electrode of the electrode pair. Similar anodic and cathodic potentials are applied independently of each other to all the other electrode pairs of the micro-electrode array. The measurement solution comprising 0.1 mol/l phosphate buffer solution (pH 7.0) with 0.1 mol/l KCl is fed through the electrode micro-chamber (micro-channel) at a flow rate of 0.8 ml/min. The basic currents of each electrode are drained independently of each other. After injection of 1 µmol/l of p-aminophenol, the rise of the oxidation currents are recorded at each anode and changes in the reduction currents are measured at each cathode (for comparison, see FIG. 1). The measurement data are mathematically processed into reduced-noise averaged measurement signals. A calibration curve is drawn by recording and processing the current changes after injection of 2.5. and 10 µmol/l p-aminophenol. At the same time, samples of alkaline phosphate with 5 mmol/l p-aminophenylphosphate are incubated in a warm measuring vessel in 1 mmol/l diethanol buffer (pH 9.8; with 0.5 mmol/l $MgCl_2$, 37° C.). After an incubation period of 1 minute, 100 µl of the reaction solution are injected into the flowing buffer of the measuring arrangement. The change in the amperometric electrode signals is individually drained and processed in the manner described supra. The enzyme activity of the measurement sample, defined as the speed of p-aminophenol formation from p-aminophenylphosphate (1 U=1 µmol/min), is then calculated on the basis of the previously established calibration curve.

In the second example, the activity of alkaline phosphatase which has been immobilized on a micro-disperse carrier, is defined with the measuring arrangement described in the previous example. The carriers are for this purpose retained in the described micro-chamber by an etched silicon grid. The formation of p-aminophenol is recorded after adding the p-aminophenylphosphate. Measuring, calibrating and evaluating are done in the same manner as in the previous example.

What is claimed is:

1. An electrochemical sensor, comprising:
   substantially dielectric first planar substrate means;
   a plurality of micro-electrode means provided on said dielectric substrate means and arranged as an array extending along a set axis, each said micro-electrode means comprising first and second sets of substantially parallel finger means of set lengths and of widths of about 1 µm and extending in a direction substantially normal to said axis, said finger means being interdigitatedly arranged and electrically insulated from each other by spacings of about 700 nm;
   single reference electrode means provided on said substrate means electrically insulated from said micro-electrode means; and
   means for selectively connecting each of said micro-electrode means and said reference electrode means to a different electrical potential.

2. The electrochemical sensor of claim 1, wherein said micro-electrode means comprise thin layers of material of the group including noble metals, potential-forming metal oxides and metal salts inserted into the surface of said substrate in a manner resulting in a planarization of said surface.

3. The electrochemical sensor of claim 2, wherein said plurality of micro-electrode means is located in micro-channel means comprising input and output flow openings, said micro-channel means comprising a groove extending between said input and output means and provided in second substrate means connected in superposition to said first substrate means.

4. The microchemical sensor of claim 3, wherein said micro-channel means comprises mechanical means for immobilizing at least one of chemically and biologically active substances.

5. The microchemical sensor of claim 1, wherein said means for selectively connecting comprises conductor strips extending from said micro-electrode means to contact means and covered by an insulating layer and wherein only said micro-electrode means and said contact means are uncovered thereby to render at least said micro-electrode means openly accessible to analytic media for electrical contacting.

6. The electrochemical sensor of claim 5, wherein said insulating layer comprises silicon oxide.

7. The electrochemical sensor of claim 5, wherein said insulating layer comprises silicon nitride.

8. The electrochemical sensor of claim 1, wherein said plurality of microelectrode means constitute working electrode means.

9. A method of utilizing an electrochemical sensor of the kind comprising substantially dielectric first planar substrate means, a plurality of micro-electrode means provided on said first dielectric substrate means and arranged as an array extending along a set axis and each comprising first and second sets of substantially parallel finger means of set lengths and widths extending in a direction normal to said axis and being interdigitally arranged in electrical insulation from each other, and further comprising reference electrode means on said first substrate means in electrical insulation from said micro-electrode means, and means for connecting said micro-electrode means and said reference electrode means to electrical potential source means for multiple measurement of the same measuring effect, comprising the steps of:

applying a different potential to each of said plurality of micro-electrode means;
   subjecting said micro-electrode means to an analyte;
   measuring at least one of the amperometric, potentiometric and impedimetric effects at individual micro-electrode means; and
   averaging said at least one amperometric, potentiometric, and impedimetric effects at each of said plurality of micro-electrode means for measuring the molecular concentration in a fluid.

10. A method of utilizing an electrochemical sensor of the kind defined in claim 9 for detecting at least one of different chemical reactions and the chronological progress of electrochemical reactions in a given substance, comprising the step of:

subjecting said micro-electrode means to said given substance;

alternatingly applying different potentials to said plurality of micro-electrode means.

11. The method of claim 10, wherein said different potentials are applied simultaneously.

12. The method of claim 10, wherein said different potentials are applied successively.

13. A method of utilizing an electrochemical sensor of the kind defined in claim 9 for measuring at least one of the flow rate on an analytic sample, the change in time of said sample and intermixing effects thereof, comprising the step of:

subjecting said micro-electrode means to said analytic sample;

measuring electrochemically active molecules of said sample at different ones of said microelectrode means by at least one of locally and temporally displaced detection.

14. A method of utilizing an electrochemical sensor of the kind defined in claim 9 for high sensitivity detection of the activity of enzymes of the kind catalyzing the release of an electrochemically reversible substance, comprising the steps of:

subjecting said micro-electrode means to an electrochemically reversible substance;

polarizing one said first and second sets of finger means of at least one of said plurality of micro-electrode means in such a manner that the reduced reaction product of said electrochemically reversible substance is oxidized, and polarizing the other of the said first and second sets of finger means of said at least one of said plurality of micro-electrode means in such a manner that the oxidized reaction product of said electrochemically reversible substance is reduced.

* * * * *